United States Patent
Wang

Patent Number: 6,107,803
Date of Patent: Aug. 22, 2000

[54] STREAMING CURRENT SENSOR

[76] Inventor: Junli Wang, 3949 Cotswold Dr., SW., Lilburn, Ga. 30047

[21] Appl. No.: 08/962,272

[22] Filed: Oct. 31, 1997

[51] Int. Cl.[7] .................................................. G01R 27/60
[52] U.S. Cl. .......................................... 324/453; 324/458
[58] Field of Search ........................... 73/864.16, 864.35; 324/453, 445, 458

[56] References Cited

U.S. PATENT DOCUMENTS

| | | |
|---|---|---|
| 3,184,973 | 5/1965 | Bradley . |
| 3,365,376 | 1/1968 | Weyland . |
| 3,368,144 | 2/1968 | Gerdes . |
| 3,368,145 | 2/1968 | Gerdes . |
| 3,369,984 | 2/1968 | Gerdes . |
| 3,526,827 | 9/1970 | Cardwell . |
| 3,614,602 | 10/1971 | Ciotti . |
| 3,746,988 | 7/1973 | Ford et al. . |
| 3,812,722 | 5/1974 | Soudelier . |
| 3,857,088 | 12/1974 | Vesely et al. . |
| 3,917,451 | 11/1975 | Groves et al. . |
| 3,943,771 | 3/1976 | Handa et al. . |
| 3,993,945 | 11/1976 | Warmoth et al. . |
| 4,100,491 | 7/1978 | Newman, Jr. et al. . |
| 4,269,064 | 5/1981 | Johnson et al. . |
| 4,297,640 | 10/1981 | Moore . |
| 4,446,435 | 5/1984 | Canzoneri . |
| 4,449,101 | 5/1984 | Canzoneri et al. . |
| 4,566,949 | 1/1986 | Berger . |
| 4,609,874 | 9/1986 | Reich . |
| 4,631,967 | 12/1986 | Welker . |
| 4,704,256 | 11/1987 | Hood et al. . |
| 4,713,618 | 12/1987 | Carlson et al. . |
| 4,769,608 | 9/1988 | Bryant . |
| 4,816,508 | 3/1989 | Chen . |
| 4,820,990 | 4/1989 | Moore ...................................... 324/453 |
| 4,825,169 | 4/1989 | Carver . |
| 4,901,024 | 2/1990 | Miyake et al. . |
| 4,961,147 | 10/1990 | Moore ...................................... 324/453 |
| 4,988,948 | 1/1991 | Francard . |
| 5,119,029 | 6/1992 | Bryant ...................................... 324/453 |
| 5,121,061 | 6/1992 | Schwab . |
| 5,121,062 | 6/1992 | Bean et al. . |
| 5,202,016 | 4/1993 | Church ...................................... 324/453 |
| 5,220,283 | 6/1993 | Dentel . |
| 5,408,185 | 4/1995 | Krah ...................................... 324/453 |

OTHER PUBLICATIONS

Chemtrac Systems, Inc., Precise Water Treatment Control Brochure, Feb. 1988.
Chemtrac Systems, Inc., Model 2000 XR Brochure, Jan. 1992.
Hach Company, Model 2000 XR Brochure, Jan. 1993.
Milton Roy, Instruction Manual For Coagulant Control Center, Jul., 1987.

*Primary Examiner*—Josie Ballato
*Assistant Examiner*—Jose M. Solis
*Attorney, Agent, or Firm*—Technoprop Colton LLC

[57] ABSTRACT

A streaming current sensor on which the placement of the sample outlet lower on the vertical axis than the sample inlet so as to increase the accuracy, reliability, and sensitivity of the sensor in comparison to those of the prior art, by enabling contaminants within the sample fluid to be removed from the buffer space before coming into contact with the sensing electrodes. The sensor further has a buffer space enabling the fluid to become a homogenous mixture of sample fluids before contacting the electrodes, thus increasing signal stability.

3 Claims, 2 Drawing Sheets

STREAMING CURRENT SENSOR

FIELD OF THE INVENTION

The present invention relates generally to a detector for detecting and measuring the streaming current of a fluid through a flow channel, and more specifically to a streaming current detector of improved sensitivity which is configured so as to prevent particles within the fluid from interfering with the streaming current detection means.

BACKGROUND OF THE INVENTION

Most waters contain ions and other charged species such as colloids. When such waters flow over or through flow channels, a zeta potential forms on the surfaces of the flow channels. When the flow channel surface, in the presence of charged species in water, is moved past a pair of electrodes, a current is generated. This current called the streaming current, and it is proportional to the net charge density of the water flow.

Measuring the streaming current is useful in controlling the amount of chemicals needed to add to fluids for various chemical processes, such as treating water for consumption or disposal. The theory of operation of such streaming current sensors is discussed extensively in U.S. Pat. Nos. 3,368,145 and 4,961,147, incorporated herein by reference. As discussed in those and other patents, a primary use of streaming current sensors is to determine whether chemically treated water is safe for consumption. For example, to make water clean enough for use, treatment chemicals are employed to change the charge density of the water so that contaminants in the water will form aggregates and settle out of the water as a floc. In particular, raw water that is usually negatively charged is processed with coagulant chemicals such as alum to reduce the negative charge. In most, if not all cases, it is economically desirable to minimize the use of the chemicals for floc formation.

Once water has been chemically treated, any floc which forms has a tendency to stick to any surface it comes into contact with, especially to horizontal surfaces. If floc is allowed to build up on a surface disposed proximate a probe in which the streaming current is being measured to evaluate the charge density of a flow stream, the sample will give an unreliable reading of the streaming current. Most successful streaming current sensors use a piston-electrode chamber configuration. Attempts have been made to keep the probe and its electrodes clean during operation. Canzoneri et al., U.S. Pat. No. 4,446,435, uses an ultrasonic cleaner attached to a probe to clean the area around the probe during operation. Ultrasonic cleaning does tend to remove colloidal particles from the surfaces of the piston-electrode chamber where measurements upon a sample are made; however, this method of introducing the sample flow into the bottom of the housing of the probe and discharging the sample flow from the housing near the top of the probe works against the natural flow of the floc with the result that the sample flow tends to be self-contaminating. Canzoneri attempted to rectify this result in the invention disclosed U.S. Pat. No. 4,449,101. In this improvement, a periodic wash is included which a cleaning fluid was backflowed into the piston-electrode chamber. Although this backflow also helped to alleviate the contamination problem, its inclusion also made the indicator system considerably more complicated.

Gerdes, U.S. Pat. No. 3,368,145, discloses a device in which the sample stream is introduced at the top of the probe and discharged downwardly from the side of the probe. However, Gerdes allows the sample stream to enter a reservoir about the piston electrode chamber within the probe so that some settling of floc and other particles tends to occur before the sample flows into the piston-electrode chamber. This causes difficulty in use of the apparatus under field conditions, resulting in erratic and erroneous measurements after only a few hours field service.

Moore, in U.S. Pat. Nos. 4,297,640 and 4,961,147, discloses units which attempt to reduce noise which is generated in the signal due to a buildup of floc near the top of the upper electrode. To minimize these noise effects, Moore places a grounding guard electrode above the two sensing electrodes, between the sensing electrodes and the point of floc buildup. This approach reduces the current that could have been produced in the absence of a grounding electrode, resulting in a weaker signal. Further, the guard electrode, while effective, does not completely eliminate all potential galvanic interferences.

Bryant, U.S. Pat. No. 4,769,608 discloses a vertical tubular flowpath in which the test flow stream constantly washes a transverse passageway to prevent contaminant accumulation. The sample is sucked into capillary sized channels within a piston-electrode chamber. The sample flows over the entrances to the capillary-sized channels with sufficient force to remove any floc that may accumulate. Bryant et al., U.S. Pat. No. 5,119,029, improves upon the invention of U.S. Pat. No. 4,769,608 by providing a streaming current sensor in which the holder for the electrodes can be removed and replaced quickly and easily.

Despite the numerous improvements made by the prior art, only limited improvement in long-term stability and sensitivity has been made over the earlier inventions. Unfortunately, the long term stability and sensitivity of currently known sensors are not as good as is sought after in industry. The sensors of the prior art locate the upper end of the flow path member exposed or vicinal to the flow liquid stream passageway (U.S. Pat. Nos. 4,961,147 and 5,119,029). It is believed in the art that this structure will keep the electrodes and the dielectric surface proximate to those electrodes free from floc buildup which would otherwise decrease the sensor's sensitivity. While partially correct, this belief fails to recognize that the sample liquid passing through the passageway is not homogeneous. This causes the sensor signal to fluctuate (under stable conditions, the second decimal digit may fluctuate in currently known sensors) and contributes to the poor stability of the sensors.

Further, sensors known in the art suffer from reduced sensitivity. The instrument's sensitivity deteriorates as the instrument operates over a period of time. The main cause behind the problem is that there is no reasonable passageway available to allow contaminants (floc for example) to exit the flowpath member before they stick to sensing electrodes and the dielectric surface proximate to these electrodes.

Most improvements in this field have been directed to self cleaning (U.S. Pat. No. 5,119,029) or employment of a third grounded electrode to collect contaminants (U.S. Pat Nos. 4,297,640 and 4,961,147). However, the sensors of the prior art mainly use passive means to handle contaminants. That is, they first allow contaminants stick to the instrument's sensitive parts, then they take some action to remove them. It would, therefore be highly advantageous to provide a sensor in which the accumulation of contaminants is prevented, thereby maintaining a high level of stability and sensitivity over a long period of time.

BRIEF SUMMARY OF THE INVENTION

A primary of the present invention is to provide a streaming current detector having a buffer space of defined size coupled with offset inlets and outlets so that contaminants do not build up on the surface of the electrodes.

Briefly, the present invention is a very stable and reliable detector for measuring the streaming current of a fluid such as water or wastewater, that can operate over long periods of time without losing stability or sensitivity. In this detector, the buffer provides enough space for contaminants/sands to follow an oblique trajectory movement with down direction, and the outlet is positioned within the trajectory path so that contaminants/sands exit the buffer from its outlet before contaminants/sands have any chance to get into sensor measuring parts.

More specifically, the invention is an improved apparatus useful in determining the electrical charge condition in a flowable liquid media containing a mildly conductive liquid electrolyte and electrical charge influencing species, particularly electrical charge influencing species which are electrically non-conductive themselves but on whose surfaces electrical charges collect. From U.S. Pat. No. 3,368,145, the old parts of this apparatus are known to comprise a tubular flow path member, or cylinder, open at one end and having electrically insulating walls. A pair of spaced apart sensing electrodes made of the same metal, with one of the electrodes taught as being at least near the closed end of the flow path member and the other electrode being at least near the open end of the flow path member. A block-like reciprocating member, also with electrically insulating walls, is taught as being located at least partially within the tubular flow path member to cause liquid located therein to flow to and fro in the flow path member in a repetitive manner. Such a block-like member can be a piston loosely fitted and slidably mounted in said flow path member in a repetitive manner, or it can be a piston with lands slidably mounted in said flow path member. Means are taught as being coupled to said electrodes for amplifying and utilizing any electrical signal induced across said electrodes. The flow path member is disposed so that a continuously different sample of the flowable liquid media can be passed in and out of the cylinder in the space between the calls of the tubular flow path member and the walls of the block-like reciprocating member past the sensing electrodes.

The improvement of the present invention comprises the location of the sample outlet on the opposite side of the buffer space from the sample inlet and disposed lower than the sample inlet, rather than at the same height. Specifically, the horizontal axis of the sample outlet is lower than the horizontal axis of the sample inlet. The distance on the vertical axis between the centerline of the sample inlet and the centerline of the sample outlet is a function of the oblique trajectory movement of the contaminants/sands in the sample and the width (or diameter) of the buffer space contained within the flowpath member. This arrangement places the sample outlet within the contaminant's trajectory path and causes the contaminants to exit the buffer space before coming into contact with the electrodes or other sensitive components of the sensor.

A further improvement of the present invention involves the size of the above-mentioned buffer space. The buffer space allows the mixing of entering sample fluid to result in a homogenous sample, thereby greatly increasing signal stability. The buffer space further makes off-line calibration possible, something impossible with prior art sensors.

DESCRIPTION OF THE PREFERRED EMBODIMENTS

Figure 1:
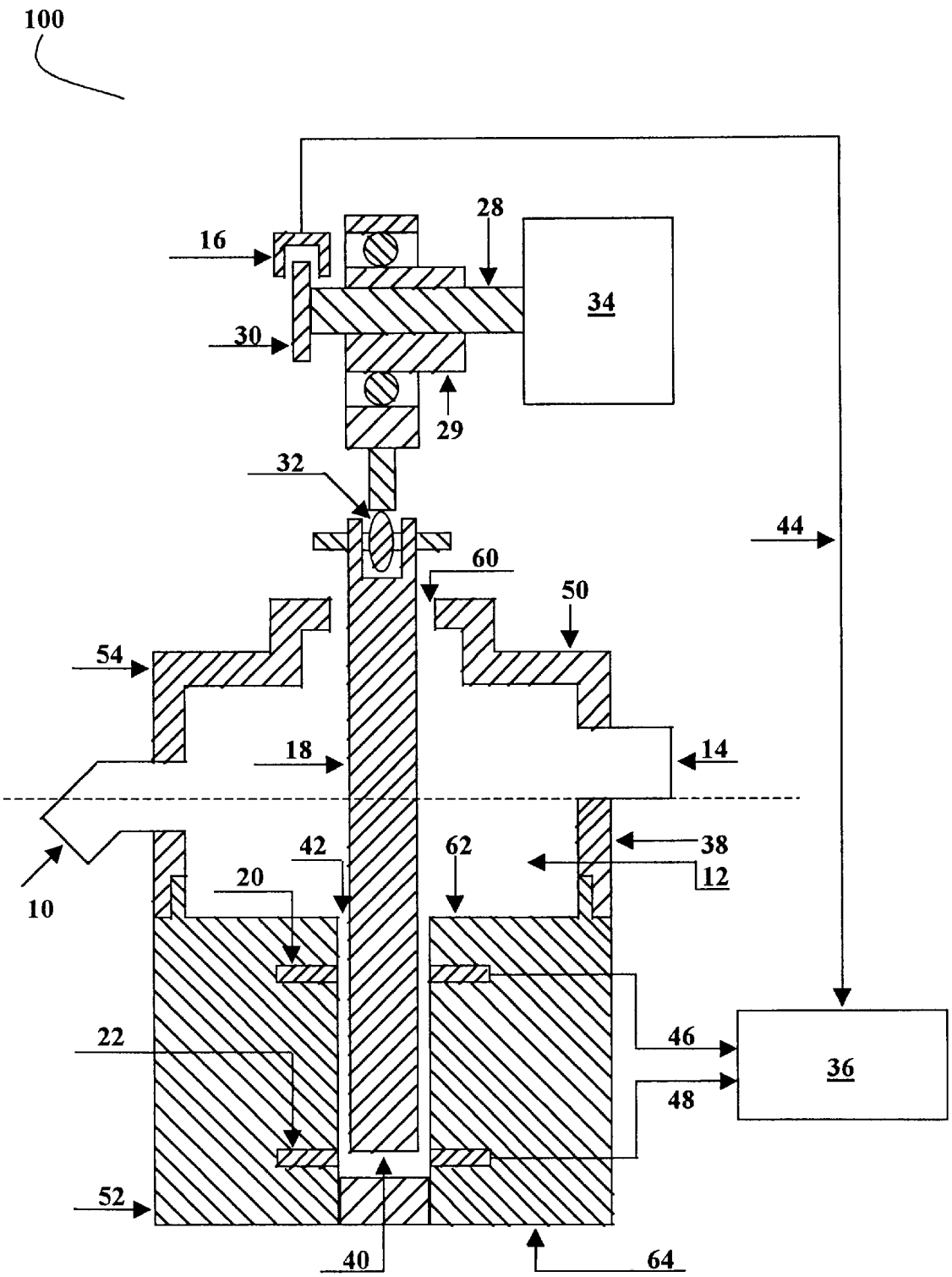
FIG. 1 is a partially diagrammatic, sectional elevation of a streaming current sensor make in accordance with the present invention.

Referring to the figures, in which like reference numerals designate like parts throughout the two views, there is shown an apparatus in accordance with the present invention for determining a function of the electrical charge condition in a flowable media containing electrical charge influencing species.

Figure 2:
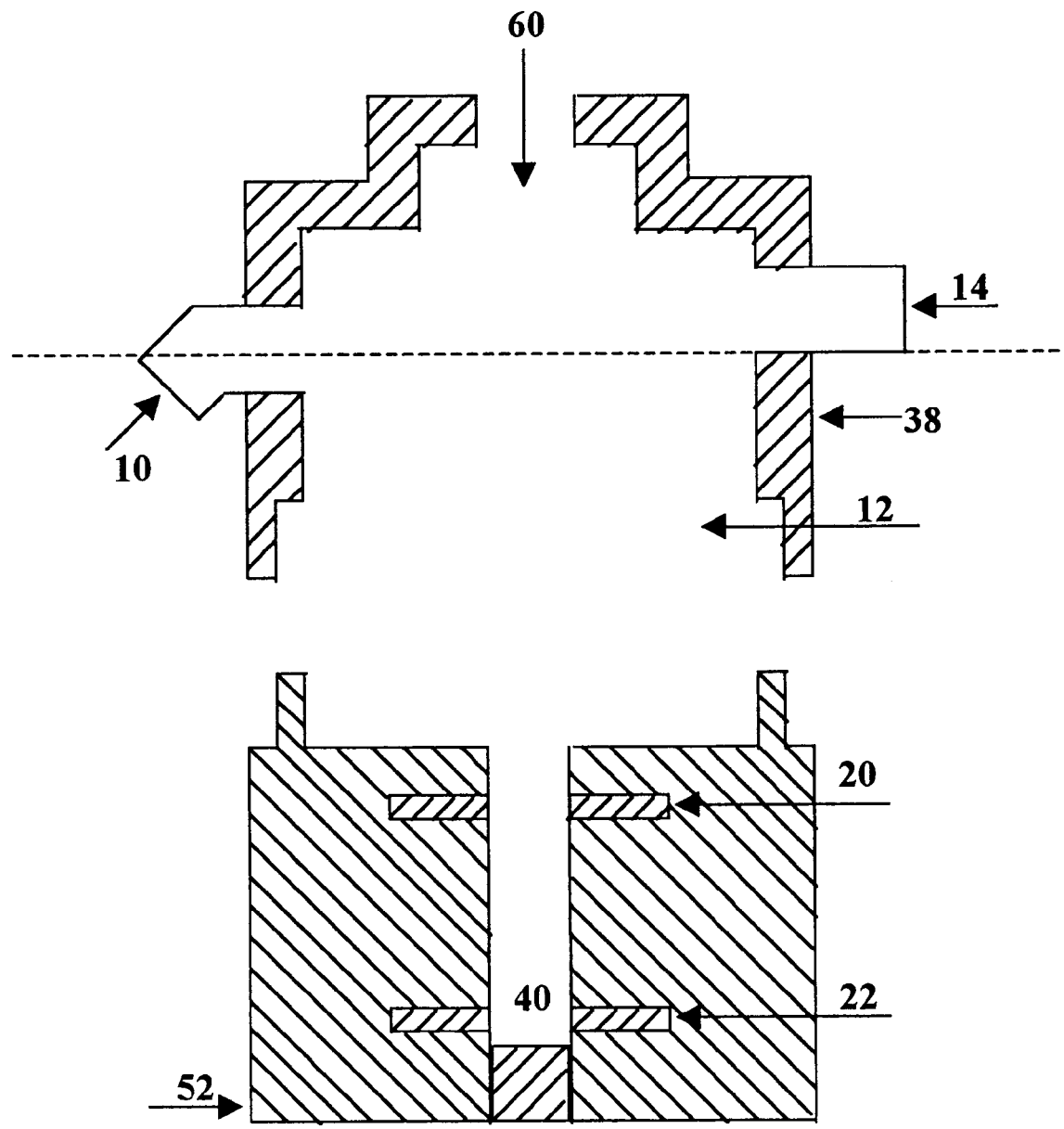
FIG. 2 is a partially diagrammatic, sectional elevation of the buffer and sensing portions of the streaming current sensor of FIG. 1.

As illustrated in FIGS. 1 and 2, the apparatus, which is indicated generally by the numeral 100, comprises a hollow flow path member 50, defining a buffer space 12 therein. The flow path member 50 can be one integral piece or, preferably, can comprise a separate buffer member 54 and sensing member 52. If the flow path member 50 comprises a separate buffer member 52 and sensing member 52, then members 54, 52 are secured together to define the buffer space 12, therebetween. Buffer member 54 and sensing member 52 preferably are slidably attached to each other, but may be attached in any known manner, such as welding, soldering, screw thread, and the like.

Sensing member 52 is a generally cylindrical structure which contains an axial bore 40 extending from the inner surface 62 of sensing member 52 to, or near to, the outer surface 64 of sensing member 52. The inner surface 62 of sensing member 52 is the surface which is located within bore 40 when sensing member 52 is secured to buffer member 54. Outer surface 64 of sensing member 54 is the surface opposite inner surface 62 and generally defines the bottom of the sensor 100.

At least two electrodes 20, 22 are inset in the wall of bore 40. Electrodes 20, 22 have electrical lead lines 46, 48, respectively, leading through sensing member 52 to a data processing circuit 36. Electrodes 20, 22 are spaced apart from each other so that electrode 20 is close to the top of bore 40, that is closer to inner surface 62, and electrode 22 is close to the bottom of bore 40, that is closer to outer surface 64. Electrodes 20, 22 are electrically insulated from one another by sensing member 52, which is manufactured from an electrically non-conductive material, and are only electrically connected by the fluid in bore 40.

Piston 18 is loosely fitted in bore 40. At least the outside surface of piston 18 is electrically non-conductive. The diameter of piston 18 is preferably about 95% of the diameter of the most narrow portion of bore 40. Piston 18 passes through upper opening 60 of the flow path member 50, which is the upper portion of buffer member 54 or a separate member attached to the upper edge of buffer member 54, from the buffer space 12 to motor 34 as discussed below.

As shown in FIG. 1, it is preferred that buffer member 54 and flow path member 50 be a single structure or two members securely attached to each other. The upper opening 60 is sealed through a fitting (not shown) screwed into the opening 60, or by any other well known means, preventing communication between buffer space 12 and the ambient.

Flow path member 50 is generally cylindrical member (or the buffer member 54, if separate) which comprises a sample inlet 14 opposite a sample outlet 10 about the cylindrical portion. Sample outlet 10 is located lower on the horizontal axis (shown as a dashed line on FIGS. 1 and 2) than sample inlet 14, and is thus, in the arrangement shown in FIG. 1, closer to sensing electrodes 20, 22. Horizontal axis is perpendicular, or as near to perpendicular as possible, to the long axis of piston 18 and the direction of piston 18 travel through buffer space 12 and bore 40. The magnitude of the distance by which sample outlet 10 is lower than sample inlet 14 is, a function of the flat trajectory of the contaminants in the sample fluid and buffer space 12 width (or diameter). Fluid is introduced to the sensor 100 through sample inlet 14 at a constant 5 gallons per minute (gpm) rate by a pump (not shown). Although flow rates higher and lower than 5 gpm can be used, such as in the 3 gpm to 7 gpm range, the industry uses 5 gpm as a standard. Using a flow rate of 5 gpm, the diameter of buffer space 12 and the vertical offset of sample inlet 14 and sample outlet 10 have a non-complex relationship and each can be selected based on the selection of the other, without undue experimentation by one of ordinary skill in the art.

During operation, contaminants (floc) contained in the fluid enter the buffer space 12 through sample inlet 14. These contaminants, depending on fluid flow, will continue along a trajectory according to well known principles of physics. Due to the effects of gravity and fluid dynamics, this trajectory will be in a downward direction. Contrary to the prior art, which located the inlet and outlet opposite each other at equal heights, the present invention locates the sample outlet 10 lower than the sample inlet 14 so that the sample outlet is within the trajectory path of the contaminants. Therefore, the horizontal centerline or axis of the sample outlet 10 must be lower than the horizontal centerline or axis of the sample inlet 14. This arrangement facilitates removal of the floc from the flow path member 50 before it accumulates on or near the electrodes 20 and 22. In addition to improving sensor sensitivity, the disclosed novel placement of the inlet 14 and outlet 10 relative to each other improves the stability of the sensor by lowering the internal pressure of the fluid.

During operation of the sensor 100, shaft 28 and offset cam 29 are rotated by synchronous motor 34 at a constant speed. Offset cam 29 acts upon piston 18. Piston 18 is forced into repetitive upward and downward motions by the action of synchronous motor 34, shaft 28, offset cam 29, and connecting means 32. Disk element 30 is affixed to shaft 28 and rotates within optical sensor 16. As piston 18 is reciprocated, liquid is forced in and out of bore 40 by the combined action of gravity and hydraulic forces caused by the reciprocating piston 18. Liquid from this flow is forced at a high velocity in and out of the open space 42 between piston 18 and bore 40. Hence, this liquid necessary flows past and contacts electrode 20 and electrode 22. This flow causes what is referred to as a streaming potential to exist between electrodes 20 and 22 and a streaming current to flow between electrodes 20 and 22 and through electrical lead lines 46 and 48. The streaming potential and streaming current are electrical in nature and are a function of the electrical charge on the non-conductive particles in the fluid. The streaming current and potential are proportional to this electrical charge and alternate at the same frequency as the reciprocating frequency of piston 18.

Data processing circuit 36 processes the alternating current (A.C.) electrical signals so that they become direct current (D.C.) signals which are a function of the electrical charge conditions of the fluid. Electrical conduction line 44 connects the optical sensor 16 to data processing circuit 36 so that the A.C. signals produced in electrical lead lines 46 and 48 by the reciprocating piston 18 driven by motor 34 can be synchronously demodulated to D.C. electrical signals by the data processing circuit 36. This is basic knowledge well-known by one of ordinary skill in the art. Processing circuit 36 measures the streaming current and outputs this information through typical and known output means (not shown).

The effect of buffer space 12 width (or diameter) in relation with signal stability and sensor sensitivity can be represented by the empirical equation:

$$BS = C \, (STBLTY/SNSTVTY) \qquad (1)$$

wherein:
　STBLTY represents the signal stability;
　SNSTVTY represents sensor sensitivity;
　BS represents the volume of the buffer space 12; and
　C is a constant.

From this Equation (1), we can see that it is unreasonable to require stability and sensitivity to be maximized simultaneously. However, if a buffer space 12 of sufficient width (or diameter) is provided to a streaming current detector 100, both stability and sensitivity will be greatly improved. It has been found that a larger buffer space 12 will result in a sensor 100 with increased stability and decreased sensitivity, and a smaller buffer space 12 will result in a sensor 100 with decreased stability and increased sensitivity, according to Equation (1). As such, one of ordinary skill in the art can construct a sensor 100 of a desired stability or sensitivity, or the best combination of the two, in relation to the buffer space 12 volume, without undue experimentation.

Buffer space 12 defined within the flow path member 50 causes fluid entering the buffer space 12 from sample inlet 14 to mix with old sample liquid for a period of time ($\Delta t$) before the mixed sample liquid contacts sensing parts. During this period, the reciprocating movement of the piston 18 mixes a portion of the entering fluid with fluid that has yet to exit through the sample outlet 10 to result in a homogeneous sample before it contacts the electrodes 20 and 22. The sensor 100, and particularly buffer space 12, sample inlet 14, and sample outlet 10, are configured such that approximately 85% of the fluid entering buffer space 12 through sample inlet 14 flows through buffer space 12 to sample outlet 10 and exits the sensor 100. Thus, approximately 15% of the fluid entering buffer space 12 is forced into bore 40 by the action of piston 60. This amount of fresh fluid is sufficient to give a proper reading of the streaming current to the fluid. This 15% of the fluid entering buffer space 12 eventually exits buffer space 12 through sample outlet 10. Preferably from 10% to 20% of the fluid entering buffer space 12 does not immediately exit through sample outlet 10 and is used for the streaming current detection. Amounts less than about 10% decrease sensitivity and amounts over 20% do not significantly increase sensitivity.

The buffer space 12 further makes off-line sensor calibration possible. The buffer space 12 is able to hold an amount of sample for calibration purposes, which enables the isolated instrument reading values to accurately reflect the amount of suspended particles expressed in NTU of the fluid presently within the buffer space 12. Because the sensors of the prior art do not provide a buffer space 12 such as that of the present sensor 100, they are unable to calibrate off-line in that they must read values at different times as the fluid flows, thereby providing only a trend of the amount of suspended particles through time.

Like the prior art sensors, the present invention may require maintenance after a certain period of operation. As explained above, the flow path member 50 of the improved streaming current sensor of the current invention 100 may optionally be divided into a buffer member 54 and a sensing member 52. Doing so simplifies maintenance and has two primary advantages: (i) the replacement of the sensor (either one, or both, of the buffer member 54 and the sensing member 52) takes just less than one minute; and (ii) off-line cleaning is easy. The buffer member 54 and the sensing member 52 of the disclosed sensor 100 are equally easy to wash and clean.

While a particular embodiment of the invention has been shown and described, various other modifications are within the true spirit and scope of the invention. The appended claims are, therefore, intended to cover all such modifications.

I claim:

1. In an apparatus for determining a function of the electrical charge condition in a flowable liquid media containing electrical charge influencing species, said apparatus having:

(a) a substantially vertical tubular flowpath member having electrically insulating walls, a top that is open, a bottom, and a fluid inlet and a fluid outlet disposed to allow the tubular flowpath member to be filled with said flowable liquid media;

(b) a sensing member comprising a central elongated vertical cavity with at least one side wall, said sensing member being located at the bottom of and in fluid communication with the tubular flowpath member so as to allow said flowable liquid media to flow into said central cavity;

(c) a piston-like reciprocating element having an outer wall that is electrically insulating and that is disposed in slideable relationship within said central cavity, said reciprocating element having a transverse cross section such that said reciprocating element fits adjacent to but spaced from said at least one side wall of said central cavity when said reciprocating element reciprocates in said central cavity;

(d) a pair of spaced apart sensing electrodes located on the side wall of said sensing member, the first of said sensing electrodes being proximal to the flowpath member and the second of said sensing electrodes being spaced below the first sensing electrode distal from the flowpath member, with both sensing electrodes so disposed as to be contacted by said flowable liquid media entering or leaving said central cavity;

(e) means for reciprocating said reciprocating element in said sensing member; and (f) means coupled to said first and second electrodes to detect and amplify any alternating component of any electrical current flowing between said first and second sensing electrodes;

wherein the improvement which comprises:

a buffer space is provided within the flowpath member, and said fluid outlet being disposed generally opposite said fluid inlet with the horizontal center line of said fluid outlet being disposed lower than the horizontal center line of said fluid inlet;

wherein said structure enables at least a portion of any particulate contaminants contained in the flowable liquid media to flow through said buffer space from said sample inlet to said sample outlet preventing at least a portion of the particulate contaminants from entering said sensing member.

2. The apparatus of claim 1, wherein a majority of any particulate contaminants contained within said flowable liquid media transverses said tubular flowpath member from said fluid inlet to said fluid outlet.

3. The apparatus of claim 1, wherein said center lines of said sample inlet and said sample outlet are substantially horizontal at a point where the flowable liquid media is introduced to said flowpath member.

* * * * *